(12) United States Patent
De Clercq et al.

(10) Patent No.: US 10,899,730 B2
(45) Date of Patent: Jan. 26, 2021

(54) PROCESS FOR PREPARING CYCLIC ESTERS FROM ALPHA-HYDROXY ESTERS AND CATALYSTS USED THEREIN

(71) Applicant: KATHOLIEKE UNIVERSITEIT LEUVEN, Leuven (BE)

(72) Inventors: Rik De Clercq, Mechelen (BE); Michiel Dusselier, Kessel-Lo (BE); Bert Sels, Westerlo (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 0 days.

(21) Appl. No.: 16/336,014

(22) PCT Filed: Sep. 25, 2017

(86) PCT No.: PCT/EP2017/074247
§ 371 (c)(1),
(2) Date: Mar. 22, 2019

(87) PCT Pub. No.: WO2018/055170
PCT Pub. Date: Mar. 29, 2018

(65) Prior Publication Data
US 2019/0367471 A1    Dec. 5, 2019

Related U.S. Application Data

(60) Provisional application No. 62/399,061, filed on Sep. 23, 2016.

(30) Foreign Application Priority Data

Dec. 19, 2016  (GB) .................................... 1621549.3

(51) Int. Cl.
*C07D 319/12*    (2006.01)
(52) U.S. Cl.
CPC .................................. *C07D 319/12* (2013.01)
(58) Field of Classification Search
CPC .................................................. C07D 319/12
See application file for complete search history.

(56) References Cited

U.S. PATENT DOCUMENTS

| | | | |
|---|---|---|---|
| 5,138,074 A * | 8/1992 | Bellis ................... | C07D 319/12 549/267 |
| 5,326,887 A | 7/1994 | Di Cosimo et al. | |
| 2015/0239863 A1 | 8/2015 | Hwang et al. | |

FOREIGN PATENT DOCUMENTS

| | | |
|---|---|---|
| DE | 4407035 A1 | 9/1995 |
| EP | 2264020 A1 | 12/2010 |
| JP | 2006104138 A * | 4/2006 |
| KR | 101467202 B1 | 12/2014 |
| WO | 9319058 A2 | 9/1993 |

OTHER PUBLICATIONS

JP-2006104138-A; WIPO English Machine Translation (2006), p. 1-19.*
Kim, W.B., "Gas phase transesterification of dimethylcarbonate and phenol over supported titanium dioxide." Journal of Catalysis 185.2 (1999): 307-313.*
Upare et al., "Design of a Heterogeneous Catalytic Process for the Continuous and Direct Synthesis of Lactide From Lactic Acid," The Royal Society of Chemistry, Green Chemistry, vol. 18, 2016, pp. 5978-5983.
International Search Report and Written Opinion from PCT Application No. PCT/EP2017/074247, dated Dec. 18, 2017.
International Preliminary Report on Patentability from PCT/EP2017/074247, dated Dec. 18, 2017.
Great Britain Search Report from GB Application No. 1621549.3, dated Jul. 24, 2017.

* cited by examiner

*Primary Examiner* — John M Mauro
(74) *Attorney, Agent, or Firm* — Workman Nydegger (57) ABSTRACT

A process for preparing cyclic esters by means of a transesterification reaction in the gas phase, comprises the steps of: (i) vaporizing a liquid solution of alpha-hydroxy esters, (ii) passing the ester vapors through a reaction zone containing a solid catalyst and (iii) recovering the cyclic esters from the gaseous product stream; and wherein the solid catalyst comprises at least one metal of titanium (Ti) and Zirconium (Zr), and a SiO2 support, and wherein said metal is chemically bound to the SiO2 support through M-O—Si chemical bonds.

26 Claims, 4 Drawing Sheets

PROCESS FOR PREPARING CYCLIC ESTERS FROM ALPHA-HYDROXY ESTERS AND CATALYSTS USED THEREIN

TECHNICAL FIELD

In general the invention concerns a process for preparing cyclic esters selectively from alpha-hydroxy esters and catalysts used therein. Said cyclic esters may be used as starting products for the preparation of polymers such as for example polyesters and bioplastics.

BACKGROUND

Cyclic esters are useful compounds that can be polymerized into polymeric materials such as biopolymers. An example of such a biopolymer is polylactic acid or polylactide (PLA). Recently, PLA is considered as a biodegradable plastic and a benign substitute for petrochemical-based plastics. Therefore, biopolymers such as PLA are of use in general polymer applications such as packaging materials, coatings and fibers, as well as in biomedicine, e.g. sutures and drug delivery systems.

To use biopolymers for the aforementioned applications, it is required for the polymer to have a high molecular weight and control over optical purity (L- or D-optical isomer). Therefore, these polymers are typically made from cyclic esters such as lactide through a so-called ring opening polymerization instead of a direct polycondensation of hydroxy acid monomers.

Cyclic esters are usually prepared by condensing hydroxy acids to an oligomeric prepolymer under reduced pressure and high temperatures. Then, the prepolymer is depolymerized in a second stage, to yield a cyclic ester through a so-called backbiting reaction, also under reduced pressure and high temperature.

Typical catalysts proposed for the back-biting reaction include zinc oxide (DE 267826 C and EP 0264926 B), Pb-oxides (DE 1543958 A) and tin compounds, such as $Sn(octanoate)_2$ and SnO (U.S. Pat. Nos. 5,247,058 A and 5,214,159 A), which are not recovered in the process.

The above-stated method is disadvantageous as (i) it is a two-step process where both steps require reduced pressures and high temperatures resulting in high energy costs, (ii) the catalyst is not recycled and (iii) racemization occurs to unwanted optical isomers, of which the uncontrolled incorporation in the final polymer chain can be detrimental for its performance.

WO 2014/122294 describes a method for producing cyclic esters by contacting an aqueous solution of a hydroxycarboxylic acid with an acidic zeolite in an organic solvent. EP 2 264 020 B1 describes a process for producing lactide by refluxing a solution of esters of lactic acid in a solvent in the presence of a homogeneous catalyst. Both processes require refluxing a solution of hydroxy acids or esters thereof in an organic solvent. This requires extensive energy input and impedes upscaling to a continuous production method. The use of homogeneous catalysts is also disadvantageous as they might be difficult to recover for reuse. Therefore, it would be more advantageous to develop a continuous process for the production of cyclic esters in the vapor phase using heterogeneous catalysts.

WO 92/00292 describes a method for producing dimeric cyclic esters in the vapor phase in the presence of a solid acid catalyst by thermolysis of alpha-hydroxycarboxylic acids. EP 0 549 698 B1 and US00/533,2839A describe a similar method for producing lactide from an aqueous lactic acid feed, where said feed is vaporized and passed through a reaction zone containing a catalyst and after which lactide, water and unreacted aqueous lactic acid feed can be withdrawn. WO 2013/160485 A1 describes a method for the production of lactide from a concentrated lactic acid solution, enriched in oligomers, where said solution is heated under reduced pressure and passes a reaction zone containing a heterogeneous catalyst. US 2015/023986 A1 describes a method for directly producing lactide by subjecting lactic acid to a dehydration reaction in the presence of a tin catalyst.

The state-of-the-art vapor phase methods share the disadvantage that they require the use of a diluted aqueous hydroxy acid feed. For aqueous solutions of lactic acid for example, it is well known that an equilibrium exists between lactic acid and its oligomers, depending on the concentration of the lactic acid solution (Vu et al., Fluid phase equilibria, 236 (2005), 125). Moreover, acids are typically not very volatile, requiring high temperatures and/or reduced pressures, and strong dilution by an inert carrier substance such as $N_2$ to bring them into the vapor phase. In addition, at high temperatures, the acidic group of the hydroxy acid might catalyze unwanted side reactions such as decarboxylation or dehydration of the hydroxyl group. Finally, it is known that water can act as a catalyst for the unwanted racemization of cyclic esters that have optical isomers such as lactide (Feng, Polymer degradation and stability, 96 (2011), 1745).

Therefore, it would be more advantageous to use esters of alpha-hydroxy acids as a feedstock for the continuous production of cyclic esters, in the vapor phase. Esters of α-hydroxy acids do not show spontaneous oligomerization in concentrated solutions (e.g. in alcoholic media) and can even be fed pure. On top of that, they are more volatile than their corresponding acids. Therefore, higher concentrations of the feed ester in the vapor phase are possible, up to 100%, and simultaneously, less energy is required for vaporization as no water has to be vaporized together with the acids. Next, esters are chemically more stable than acids due to the absence of an acidic group and are thus less prone to autocatalytic side reactions. Finally, hydroxy acids produced by fermentation, such as lactic acid, are commonly purified by converting the acids to alkyl esters, distilling the esters and subsequently hydrolyzing the esters back to their corresponding acids. (Dusselier et al., Energy & Environ Sci., 6 (2013), 1415) The direct use of esters for the production of cyclic esters would therefore not require an additional hydrolysis step during the purification of the feed and integrate well with current lactic acid purification schemes.

In view of the foregoing, it is an object of the present invention to produce cyclic di-esters with a high selectivity (≥75%), directly from alpha-hydroxy esters in the vapor phase using a suitable catalyst.

SUMMARY OF THE INVENTION

The present inventors have now surprisingly found that all of these objectives can be obtained by the process of the present invention.

The present invention concerns a process for directly producing cyclic esters from alpha-hydroxy esters in the gas phase, comprising the following steps:
 (i) vaporizing a liquid solution of alpha-hydroxy esters
 (ii) passing the ester vapors through a heated reaction zone containing a solid catalyst capable of selectively catalyzing the cyclization of the alpha-hydroxy esters to the corresponding cyclic ester;

(iii) recover the cyclic ester from the gaseous product stream;

and wherein the solid catalyst comprises at least one metal (M) of Mendeleev group II, III, IV or V of the Periodic Table, preferably titanium (Ti) or zirconium (Zr), and wherein said metal is chemically bound to a $SiO_2$ containing support through metal-oxygen-silicon (M-O—Si) chemical bonds as described herein.

More specifically, the term "chemically bound" is used to denote the presence of M-O—Si chemical bonds between the metal and the $SiO_2$ support, wherein M constitutes a metal of Mendeleev group II, III, IV or V of the Periodic Table, preferably titanium (Ti) or zirconium (Zr), O stands for oxygen and Si stands for silicon.

DETAILED DESCRIPTION OF THE INVENTION

Some of the following abbreviations might be preceded by a "L-", "D-" or "meso-" prefix, which designates the optical isomers of the product that follows this prefix.
MLA: methyl lactate
$ML_2A$: methyl lactoyl lactate, viz. the linear dimer of MLA.
LD: lactide
WHSV: weight hourly space velocity, defined as:

$$WHSV = \frac{flowrate}{m_{cat}},$$

wherein the flowrate is expressed as mass flow of alpha-hydroxy esters per time unit and $m_{cat}$ stands for the mass of the catalyst used. The unit of the WHSV is $h^{-1}$.
W/F: contact time of the gas going over the catalyst, with unit $g_{catalyst}$ h $mol_{gas}^{-1}$.
$MO_x/SiO_2$: catalyst whereby the $MO_x$ active compound is supported on the surface of an amorphous $SiO_2$ gel.
$MO_x$—$SiO_2$: catalyst whereby the $MO_x$ active compound is distributed within the bulk matrix of the $SiO_2$ support.
$MO_x$/MCM-41: catalyst whereby the $MO_x$ active compound is supported on the surface of a $SiO_2$ support having the MCM-41 ordered mesoporous structure.
The degree of racemization: when an enantiomerically pure starting solution of a certain alpha-hydroxy ester is used, which may lead to cyclic ester products of which different optical isomers exist, the degree of racemization is defined herein as the percentage of the meso-optical isomer (L,D- or D,L-optical isomer) of said product, compared to the total amount of all isomers of said product.
wt %: the weight percentage of the active compound of a catalyst is defined as the weight of the metal's corresponding oxide ($MO_x$), compared to the total weight of the catalyst.
$S_{BET}$: specific surface area of the catalyst according to the Brunauer-Emmett-Teller theory.

In present application an element of Mendeleev group II of the Periodic Table means any element selected of beryllium (Be), magnesium (Mg), calcium (Ca), strontium (Sr) or barium (Ba). In present application an element of Mendeleev group III of the Periodic Table means any element selected of aluminium (Al), gallium (Ga), indium (In), scandium (Sc), yttrium (Y), lanthanum (La) or cerium (Ce). In present application an element of Mendeleev group IV of the Periodic Table means any element of titanium (Ti), zirconium (Zr), tin (Sn), lead (Pb) or hafnium (Hf). In present application an element of Mendeleev group V of the Periodic Table means any element of vanadium (V), niobium (Nb) or tantalum (Ta).

The present invention concerns a process for directly producing cyclic esters from alpha-hydroxy esters in the gas phase, comprising the following steps:
(i) vaporizing a liquid solution of alpha-hydroxy esters
(ii) passing the ester vapors through a reaction zone containing a solid catalyst capable of selectively catalyzing the cyclization of the alpha-hydroxy esters to the corresponding cyclic ester,
(iii) recover the cyclic ester from the gaseous product stream; and wherein the solid catalyst comprises at least one metal of Mendeleev group II, III, IV or V of the Periodic Table, and wherein said metal is chemically bound to a $SiO_2$ containing support through M-O—Si bonds as described herein.

More specifically, in the present invention, a method is provided for the direct production of cyclic esters, which includes performing a transesterification reaction in the vapor phase between two molecules of an alpha-hydroxy ester, following Chemical Formula (1), which are passed through a heated reaction zone containing a suitable catalyst as described herein, capable of selectively producing a cyclic ester, following Chemical formula (2), and releasing the corresponding alcohol, following Chemical Formula (3), as a side product, according to Reaction scheme 1.

<Reaction Scheme 1>

Wherein $R_3$ is a $C_1$-$C_6$alkyl group and $R_1$ and $R_2$ are each independently selected from hydrogen or a group selected from $C_{1-6}$alkyl; $C_{2-6}$ alkenyl; $C_{6-10}$aryl, $C_{1-10}$alkyl$C_{6-10}$arylene; $C_{6-10}$aryl$C_{1-6}$alkylene; or $C_{2-6}$ alkynyl; each group optionally substituted by one or more substituents selected from $C_{1-6}$alkyl, $C_{1-6}$alkoxy. In further embodiments, $R_3$ is a $C_{1-4}$alkyl group and $R_1$ and $R_2$ are each independently hydrogen or a group selected from $C_{1-4}$alkyl; $C_{2-4}$ alkenyl; or $C_{2-4}$ alkynyl; each group optionally substituted by one or more substituents selected from $C_{1-6}$alkyl, $C_{1-6}$alkoxy. In further embodiments, $R_3$ is a $C_{1-4}$ alkyl group and $R_1$ and $R_2$ are independently selected from hydrogen, $C_{1-4}$alkyl, or $C_{2-4}$ alkenyl. In certain embodiments, at least one of $R_1$ and $R_2$ is not hydrogen.

In certain embodiments, the alpha-hydroxy ester is a compound of Chemical Formula (1), wherein $R_3$ is a $C_{1-6}$alkyl group, $R_1$ is hydrogen and $R_2$ is a group selected from $C_{1-6}$alkyl; $C_{2-6}$ alkenyl; $C_{6-10}$aryl, $C_{1-10}$alkyl$C_{6-10}$arylene; $C_{6-10}$aryl$C_{1-6}$alkylene; or $C_{2-6}$ alkynyl; each group optionally substituted by one or more substituents selected from $C_{1-6}$alkyl, $C_{1-6}$alkoxy; preferably $R_2$ is selected from $C_1$-$C_6$alkyl, $C_2$-$C_6$ alkenyl or $C_2$-$C_6$ alkynyl; more preferably $R_2$ is $C_{1-4}$alkyl or $C_{2-4}$ alkenyl.

In preferred embodiments, the compound of Chemical Formula (1) can be selected from a group comprising $C_{1-6}$alkyl esters of lactic acid, glycolic acid, 2-hydroxy butyric acid, 2-hydroxy-3-butenoic acid and 4-methoxy-2-hydroxy butanoic acid. Preferably, the compound of Chemical Formula (1) is an ester of lactic acid, wherein $R_1$=H, $R_2$=$CH_3$ and $R_3$ is a $C_{1-6}$alkyl group, preferably a $C_{1-4}$ alkyl group and even more preferably a $C_{1-2}$alkyl group.

In another preferred embodiment, the alpha-hydroxy ester used in the present invention is methyl lactate (MLA), following Chemical Formula (1), wherein $R_1$=H, $R_2$ and $R_3$ are $CH_3$, and where the cyclic ester product is lactide (LD), following Chemical Formula (2), wherein $R_1$=H, $R_2$=$CH_3$, and where the corresponding alcohol that is eliminated is methanol.

In another preferred embodiment, the alpha-hydroxy ester used in the present invention is the L-form optical isomer of methyl lactate, denoted as L-methyl lactate (L-MLA), and where the cyclic ester product is the L,L-optical isomer of lactide, denoted L,L-lactide or L-lactide (L-LD), and where the corresponding alcohol is methanol, according to Reaction Scheme 2.

In some embodiments, the alpha-hydroxy ester used in the present invention is the D-form optical isomer of methyl lactate, denoted as D-methyl lactate (D-MLA), and where the cyclic ester product is the D,D optical isomer of lactide, denoted D,D-lactide or D-lactide (D-LD), and where the corresponding alcohol is methanol.

In some embodiments, the alpha-hydroxy ester used in the present invention is a mixture of L-methyl lactate and D-methyl lactate and where the cyclic ester product comprises a mixture of L,L-lactide, D,D-lactide and meso-lactide (consisting of L,D-lactide or D,L-lactide), and where the corresponding alcohol is methanol.

In a particular embodiment of the present invention, the transesterification reaction between two molecules of an alpha-hydroxy ester may occur directly, instantly forming the cyclic ester, or may occur through an intermediate linear dimer (Formula 4 in Reaction scheme 3), according to Reaction Scheme 3, wherein the aforementioned definitions of $R_1$, $R_2$ and $R_3$ of Reaction Scheme 1 remain valid as it comprises the same reaction.

The liquid ester feed may contain one or more types of alpha-hydroxy esters and may be diluted beforehand with a suitable solvent. In a particular embodiment, a liquid solution of only one type of alpha-hydroxy ester is used, for the preparation of a symmetric cyclic di-ester. In some embodiments, it is envisaged that a mixture of two or more types of alpha-hydroxy esters can be used, for example for the preparation of asymmetric cyclic esters (in this case, not according to Scheme 3). Preferably, the liquid ester feed is a pure solution (≥95%) of only one type of alpha-hydroxy ester.

In a particular embodiment of the present invention, evaporation of the liquid alpha-hydroxy ester feed may occur in a heated evaporation zone. In another particular embodiment, the evaporation zone to which the liquid alpha-hydroxy ester is fed, should have at least a volume capable of allowing full expansion of the liquid hydroxy ester to its corresponding vapors.

In a preferred embodiment, a carrier substance, inert at operating temperature and pressure, can be used to facilitate transport of the aforementioned ester vapors to the reaction zone for contact with the solid catalyst, and to facilitate transport of the cyclic ester products away from the reaction zone. In certain embodiments, the carrier substance may be added inside the evaporation chamber to enhance evaporation of the liquid ester feed, or may be added after the evaporation chamber, where gas mixing then occurs.

In a more preferred embodiment, the carrier substance is fed through the evaporation chamber along with the liquid alpha-hydroxy ester feed in order to facilitate the evaporation of the alpha-hydroxy esters and to produce a homogeneous gas stream comprising the inert carrier substance and vapors of the alpha-hydroxy esters, and to facilitate transport of said stream to the reaction zone for contact with the solid catalyst.

Any carrier substance may be chosen, provided that it is gaseous and non-reactive at the chosen reaction temperature and pressure. Preferably, inert permanent gases (at room temperature and a pressure of 1 atm) such as $N_2$, He or Ar or the like can be used, most preferably $N_2$ is used. A technical effect of an inert gas e.g. inert carrier substance is enhancing the evaporation of the alpha-hydroxy ester precursor. Another technical effect is aiding transport of the alpha-hydroxy ester vapors to the reaction zone containing the catalyst and transport of the product stream away from the reaction zone.

The liquid alpha-hydroxy ester feed may be fed to the evaporation chamber continuously or intermittently, using a liquid pump or the like. Accordingly, the carrier substance may also be independently added continuously or intermittently to or after the evaporation zone. In a preferred embodiment, both the liquid alpha-hydroxy ester feed and the carrier substance are fed continuously at constant flows, in order to keep a constant vapor composition over time.

The flows of the liquid alpha-hydroxy ester feed and carrier substance may be chosen independently of each other in such a way that the desired vapor composition is obtained upon mixing the carrier substance with the alpha-hydroxy ester vapors before passing said vapor mixture through a heated reaction zone for contact with the solid catalyst. The concentration of alpha-hydroxy ester vapors in the carrier substance should be at least between 0.5% and 50 mol %, particularly between 2% and 35 mol %, more preferably between 5 and 25 mol % and most preferably between 5 and 15 mol %.

In a particular embodiment, the evaporation chamber should be heated to a temperature that is high enough to allow for the full evaporation of the liquid alpha-hydroxy ester feed, with or without an inert carrier substance passing the evaporation chamber to facilitate the evaporation. In certain embodiments, the temperature of the evaporation chamber should be at least between 180-300° C., particularly between 200-260° C. and preferably between 210-240° C.

In most embodiments, there are no pressure limitations that should be used in the evaporation chamber, except that an operating pressure must be chosen so that full evaporation of the liquid hydroxy ester feed is still allowed at the chosen pressures and temperatures. In a preferred embodiment, the pressure inside the evaporation chamber is equal to or lower than atmospheric pressure. In a more preferred embodiment, the evaporation chamber operates at atmospheric pressure.

After adding the inert carrier substance to the hydroxy ester vapors, the resulting vapor mixture may or may not be additionally mixed before passing said vapor mixture to the heated reaction zone for contact with the solid catalyst.

Said heated reaction zone should contain a suitable catalyst as described herein to catalyze the transesterification reaction between two molecules of an alpha-hydroxy ester towards the corresponding cyclic ester with a high selectivity (≥75%) towards the cyclic ester.

The inventors have surprisingly found that cyclic ester synthesis can be simplified significantly by using catalysts comprising at least one metal (M) of Mendeleev group II, III, IV or V of the Periodic Table (further denoted as "active compound") and wherein said metal is chemically bound to the oxide of silicon ($SiO_2$), which serves as an inert support for the active compound.

More specifically, the term "chemically bound" is used to denote the presence of M-O—Si chemical bonds between the active compound and the $SiO_2$ support, wherein M constitutes at least one metal of Mendeleev group II, III, IV or V of the Periodic Table, O stands for oxygen and Si stands for silicon.

The inventors have surprisingly found that in particular, the presence of M-O—Si bonds between titanium (Ti), zirconium (Zr), or both and the $SiO_2$ support as described herein provides an excellent selectivity of the catalyst towards cyclic esters (≥75%), in contrast to pure or mixed oxides of metals of Mendeleev group II, III, IV, or V of the Periodic Table, which lack these M-O—Si bonds, as they only exhibit poor selectivities towards cyclic esters in the process described herein.

Thus, the catalysts described herein allow for the continuous production of cyclic esters such as lactide in a single step from alpha-hydroxy esters in the vapor phase, thus avoiding the condensation to a prepolymer and depolymerisation towards a cyclic ester.

The presence of such M-O—Si chemical bonds as described herein may be verified by conventional spectroscopic techniques, such as Fourier transform infrared spectroscopy (FT-IR), diffuse reflectance UV-VIS spectroscopy (DR UV-VIS), X-ray photoelectron spectroscopy (XPS), Raman spectroscopy or any other suitable method as described in literature, for example in: Gao et al., Catalysis Today, 1999, 51, 233.

The $SiO_2$ support may contain micropores, mesopores, macropores or a combination of any of the former and may be amorphous, crystalline, or ordered mesoporous, for example having the MCM-41, SBA-15, HMS, MSU-F or MSU-H structure (Di Renzo et al. (2002), Ordered Mesoporous Oxides, Weitkamp J. et al. (Eds.), in Handbook of Porous Solids (pp 1311-1395), Weinheim, Wiley-VCH Verlag GmbH). The active compound may be supported on the surface of the $SiO_2$ support (further denoted as "supported catalysts"), incorporated within the bulk framework of $SiO_2$ (further denoted as "gel catalysts"), or both. The active compound may also be incorporated in the crystalline framework of zeolites. The term "zeolite" as used herein refers to both natural and synthetic microporous crystalline materials based on oxides of tetrahedral elements, with at least one of these elements being Si, having a definite crystalline structure as determined by X-ray diffraction. A zeolite comprises a system of channels which may be interconnected with other channel systems or cavities such as side-pockets or cages. The channel system may be three-dimensional, two-dimensional or one-dimensional. Herein, a zeolite comprises $SiO_4$ and $XO_4$ tetrahedra, wherein X is aluminium (Al), boron (B), or a metal of Mendeleev group III and IV of the Periodic Table, capable of forming $XO_4$ tetrahedra. A zeolite may comprise a combination of different $XO_4$ tetrahedra. In a preferred embodiment, the zeolite comprises $SiO_4$ and $XO_4$ tetrahedra, wherein X is a compound of Mendeleev group III or IV of the Mendeleev table, and the zeolite contains no $BO_4$ tetrahedra.

In a preferred embodiment, the catalyst contains at least one metal of Mendeleev group II, III, IV or V of the Periodic Table and a $SiO_2$ support and wherein M-O—Si chemical bonds are present between the metal and the $SiO_2$ support. Preferably, the catalyst contains at least one metal of Mendeleev group III or IV of the Periodic table. More preferably, the catalyst contains at least one metal of Mendeleev group IV of the Periodic table. More preferably, the catalyst contains at least one metal of the group of titanium (Ti) and zirconium (Zr). Even more preferably, the catalyst contains only one type of metal of the group of titanium (Ti) and zirconium (Zr).

Most preferably, the catalyst contains titanium (Ti).

In the case of zeolites, the zeolite preferably comprises $SiO_4$ and $XO_4$ tetrahedra, wherein X is a metal of Mendeleev group III or IV of the Periodic table, and the zeolite contains no $BO_4$ tetrahedra. More preferably, X is a metal of Mendeleev group IV of the Periodic table, and the zeolite contains no $AlO_4$ or $BO_4$ tetrahedra. Even more preferably, X is Ti or Zr and the zeolite contains no $AlO_4$ or $BO_4$ tetrahedra. Most preferably, X is Ti and the zeolite contains no $AlO_4$ or $BO_4$ tetrahedra.

In certain embodiments of the present invention, the catalyst contains a metal of Mendeleev group III of the Periodic Table which has an oxidation state of +3, such as for example $Al^{3+}$, and a $SiO_2$ support and wherein M-O—Si chemical bonds are present between said metal oxide and the $SiO_2$ support. However, when trivalent metal ions such as $Al^{3+}$ are coordinated tetrahedrally with $SiO_2$, a negative charge in the framework arises, which may be neutralized by protons, which are Brønsted acidic. It is typically not preferred that the catalyst is strong Brønsted acidic as this may cause the alpha-hydroxy esters to undergo side reactions such as decarbonylation, decarboxylation or dehydration rather than forming the cyclic esters.

The catalysts described in the present invention may be made by any of the suitable methods known in the art. For example supported catalysts may be made by wet impregnation or incipient wetness impregnation of a $SiO_2$ support with a solution containing a precursor of the active compound, followed by drying and calcination to convert the precursor into the active compound and to establish the M-O—Si bonds as described herein. Gel catalysts may be made through known sol-gel methods, wherein a colloidal solution, a so-called sol, of silica and the active compound is condensed, forming a gel. The gel may be dried, forming a xerogel or aerogel and subsequently calcined to form the catalytically active M-O—Si bonds between $SiO_2$ and the active compound. Zeolite catalysts may be synthesized hydrothermally, wherein a silicon precursor and suitable precursor of the active compound are crystallized simultaneously, incorporating the active compound in the zeolite framework. Zeolite catalysts may also be made through post-treatment of commercial zeolites, for example by dealumination of a zeolite containing $AlO_4$ tetrahedra, and wherein the active compound is subsequently deposited in the framework, which after calcination result in the M-O—Si bonds as described herein. The % by weight composition of the active compound is defined as the weight percentage of the metal's corresponding oxide ($MO_x$), compared to the total weight of the catalyst, and may vary widely. In the present invention, there is no particular limitation in the content of the active compound. However, the active compound may comprise between 0.1% and 50% by weight of the catalyst, in general between 1% and 30% by weight of the catalyst, particularly between 1% and 20% by weight of the catalyst, and preferably between 1 and 10% by weight of the catalyst.

Pellet size, pore volume and total surface area may vary widely, but depend on the catalyst support. However, large surface areas are preferred, as they provide a larger surface area for the hydroxy esters to come in contact with the supported active compound.

The catalyst support may be bought commercially (e.g. $SiO_2$ gel from Alfa Aesar or Sigma-Aldrich), or may be synthesized through methods known in the art, such as for example (co-) precipitation techniques, whereby $Si(OH)_2$ can be precipitated by acidifying a sodium silicate solution, followed by filtering/washing the $Si(OH)_2$ and calcination to obtain the final $SiO_2$ structure or through common sol-gel procedures. There is no particular limitation in the form of the catalyst in the present invention, and the catalyst may have any form that can be charged in a reactor, for example, granule, pellet, injection mold, monolith, honeycomb, thin film or the like, and a proper form can be selected depending on the form of the reactor.

In certain embodiments of the present invention, the catalyst bed may consist only of catalyst particles, but the catalyst particles may also be diluted with an inert solid material, for example quartz or silicon carbide particles, to increase the catalyst bed size or to aid in heat and mass transport inside the catalyst bed.

In the process of the present invention, the temperature of the reactor zone containing the catalyst should be high enough to keep all compounds, whether it is a compound of the feed, intermediate, or product, in the vapor phase during the reaction and to effectively catalyze the cyclization of the alpha-hydroxy esters, but not too high that the resulting cyclic ester degrades thermally or catalytically. The inventors have found that increased temperatures can significantly enhance reaction rates while maintaining a high selectivity towards the desired cyclic esters at slightly higher conversions, but degradation of the cyclic ester product might occur if the contact time with the catalyst is too long. Therefore, it is advisable to keep contact times short enough at increased temperatures as to avoid thermal or catalytic degradation of the cyclic ester product. In a particular embodiment of the process of the present invention, the reaction temperature should be at least 180° C. and should not exceed 300° C. Preferably, the reaction temperature should be between 200° C. and 300° C., more preferably between 220-280° C. and most preferably between 220-260° C.

In the present invention, there is no particular limitation in reaction pressure inside the reaction zone, provided that at the chosen reaction pressure, all compounds, whether they are a compound of the feed, an intermediate, or reaction product remain in the vapor phase at that pressure. The processes described herein may be performed at or near atmospheric pressures, and are typically performed at a pressure between 0.1 and 20 bar. In particular embodiments, the processes are performed at a pressure between 0.5 and 5 bar, preferably between 0.8 and 1.2 bar.

In particular embodiments, pure isomeric forms of alpha-hydroxy esters can be used. However, it is also envisaged that in certain embodiments, a racemic mixture or other mixtures of different isomeric forms of alpha-hydroxy esters can be used. Pure isomeric forms are defined herein as isomers substantially free of other enantiomeric or diastereomeric forms of the same basic molecular structure. In particular, the term "stereoisomerically pure" or "chirally pure" used herein relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question. The term "enantiomeric excess" or "% ee" as used herein refers to the amount of an enantiomer with respect to another. It can be calculated as follows:

% ee=[([A]−[B])/([A]+[B])]×100 wherein [A] is the concentration of one of the enantiomers, and [B] is the concentration of the other enantiomer. The concentration of each of the enantiomers is, of course, expressed on the same basis, and can be expressed on either a weight or molar basis because the enantiomers have the same molecular weight. Consequently, if a mixture of enantiomers is obtained during any of the following preparation methods, it can be separated by liquid chromatography using a suitable chiral stationary phase.

The processes described herein may therefore be used for the preparation of enantiomerically pure cyclic esters. Indeed, the inventors have found that in particular embodiments of the present invention, little racemization of the cyclic ester occurs (≤7%). This means that if enantiomerically pure alpha-hydroxy esters are used in the process described herein, the resulting cyclic esters will also be relatively enantiomerically pure. Accordingly, in particular embodiments, the alpha-hydroxy esters used in the processes described herein are enantiomerically pure, with an enantiomeric excess of at least 90%, preferably at least 95%.

Lactide has two asymmetric carbon atoms so it may be obtained in three stereoisomeric forms: L,L-lactide in which both asymmetric carbon atoms possess the L (or S) configuration; D,D-lactide in which both asymmetric carbon atoms possess the D (or R) configuration; and meso-lactide (L,D- or D,L-lactide), in which one asymmetric carbon atom has the L-configuration and the other has the D-configuration.

In certain embodiments of the processes described herein, the alpha-hydroxy ester is L-methyl lactate (with an enantiomeric excess of at least 90%, preferably at least 95%, more preferably at least 98%) and the corresponding cyclic ester is L,L-lactide.

In certain embodiments of the processes described herein, the alpha-hydroxy ester is D-methyl lactate (with an enantiomeric excess of at least 90%, preferably at least 95%, more preferably at least 98%) and the corresponding cyclic ester is D,D-lactide.

In certain embodiments of the processes described herein, the feedstock is a racemic mixture (equal amounts of the L- and D-optical isomer) or any other mixture of L-methyl lactate and D-methyl lactate, and the corresponding cyclic ester is a mixture of L-lactide, D-lactide and meso-lactide, wherein the distribution of the different diastereomers depends on the initial feedstock composition and thermodynamic considerations.

In certain embodiments of the processes described herein, pure isomeric forms of alpha-hydroxy esters may be used for the production of cyclic esters, wherein the distribution of the different optical isomers of the resulting cyclic ester is determined by racemization induced by the catalyst. If the production of a mixture of different optical isomers of cyclic esters from a solution of enantiomerically pure alpha-hydroxy esters is desired, a catalyst may be used in the process of the present invention that is capable of producing cyclic esters from alpha-hydroxy esters via transesterification, as well as a controlled racemization of said cyclic esters to obtain a desired mixture of different optical isomers.

The inventors have surprisingly found that racemization of the cyclic ester product, and thus distribution of the different optical isomers in the product mixture, may be controlled by the choice of metal used in the catalyst. For example, the inventors have surprisingly found that catalysts comprising M-O—Si bonds between the metal and the support, and wherein M is titanium (Ti), show little isomerization of lactide (e.g. ≤7% meso-lactide). On the other hand, catalysts comprising M-O—Si bonds between the metal and the support, and wherein M is zirconium (Zr), show significantly more isomerization of lactide (e.g. ≤25% meso-lactide). Catalysts comprising M-O—Si bonds between the metal and the support, and wherein M is a mixture of titanium (Ti) and zirconium (Zr), show mediocre isomerization of lactide that is proportional to the ratio of Ti and Zr (e.g. ≥7 but ≤25% meso-LD).

In the case L-methyl lactate is used as starting liquid ester feed and the catalyst comprises M-O—Si bonds between the metal and the support, and wherein M is titanium (Ti), the process of the present invention provides a direct, continuous route for the preparation of L,L-lactide, characterized by relatively high yields (~40-50%) and high selectivities (≥75%). Other products in the product stream mainly include unreacted L-methyl lactate, methanol and the linear dimer L,L-methyl lactoyl lactate (ML$_2$A, Reaction Scheme 3, product (4)). The process of the present method is advantageous in that the main by-products of the product stream (MLA and ML$_2$A) are unreacted starting compounds or reaction intermediates that can be recycled back to the original feed as a liquid or as a vapor at the reactor inlet. With a supported TiO$_2$/SiO$_2$ catalyst, degree of racemization of L-lactide to meso-lactide (L,D- or D,L-lactide) is low (≤5%), whereas with a supported ZrO$_2$/SiO$_2$ catalyst, higher degrees of racemization of L-lactide to meso-lactide are obtained (≤25%). The process of the present invention is thus advantageous in that the degree of racemization of L- or D-lactide to meso-lactide can be controlled by the choice of catalyst.

The reaction mixture of the process of the present invention contains not only the cyclic ester product, but also unreacted alpha-hydroxy esters, small amounts of dimers or oligomers and alcohol, and the cyclic ester should thus be separated therefrom prior to further use. Cyclic esters, such as lactide, may be separated by conventional methods known in the art, such as distillation, (re)-crystallization, solvent scrubbing or solvent extraction. Other products in the product stream, such as unreacted alpha-hydroxy esters or alcohols, may also be separated by conventional methods known in the art, and may be recycled for reuse. For example, unreacted alpha-hydroxy esters may be recycled back to the reactor inlet, whereas the alcohols may be reused in the production of the alpha-hydroxy ester feedstock or any other suitable process.

The invention will now be illustrated by the following, non-limiting illustrations of particular embodiments of the present invention.

EXAMPLES

In the following examples, conversion (C), selectivity (S) and yield (Y), expressed in mol %, are defined as follows:

$$\text{Conversion} = \frac{\text{moles of } \alpha\text{-hydroxy ester converted}}{\text{initial amount of } \alpha\text{-hydroxy ester}} (\%),$$

-continued $$\text{Selectivity} = \frac{\text{moles of product formed} * \text{moles of } \alpha\text{-hydroxy ester incorporated in product}}{\text{moles of } \alpha\text{-hydroxy ester converted}} (\%),$$

$$\text{Yield} = \text{Conversion} \times \text{Selectivity } (\%).$$

Example 1: Production of Lactide from Methyl Lactate with a $TiO_2/SiO_2$ Catalyst In this example, a supported $TiO_2/SiO_2$ catalyst, wherein the active component (Ti) is connected to the surface of an amorphous $SiO_2$ support through Ti—O—Si bonds, was tested for the synthesis of lactide (LD) from L-methyl lactate (L-MLA). The catalyst was prepared by an incipient wetness impregnation technique of an amorphous $SiO_2$ gel (Alfa Aesar, $S_{BET}$=287 m² g⁻¹ and pore volume=0.913 cm³ g⁻¹). For this, a suitable amount of metal precursor (Ti-isopropoxide) was dissolved in a solvent (isopropanol). The amount of metal precursor was chosen so that the resulting supported metal oxide ($TiO_2$) phase would comprise approx. 5% by weight of the final catalyst. The amount of solvent was chosen so that the total volume of impregnation liquid (metal precursor and solvent) was approximately equal to the total pore volume of the catalyst. The $SiO_2$ gel was dried at 100° C. overnight beforehand to remove any excess water from the pores. The impregnation liquid containing the metal precursor was then added to the dried $SiO_2$ gel while often stirring the powder using a spatula. After all impregnation liquid was added to the $SiO_2$ gel, the impregnated $SiO_2$ was stirred for two more minutes and was then dried in an oven at 80° C. for at least 8 hours. Afterwards, the powder was calcined at 500° C. for 4 hours with a heating rate of 5° C. min⁻¹ to obtain the active $TiO_2/SiO_2$ catalyst containing the necessary Ti—O—Si bonds. The fine catalyst powder was then pressed into pellets and sieved to obtain uniform pellets of 250-500 μm.

Figure 1:
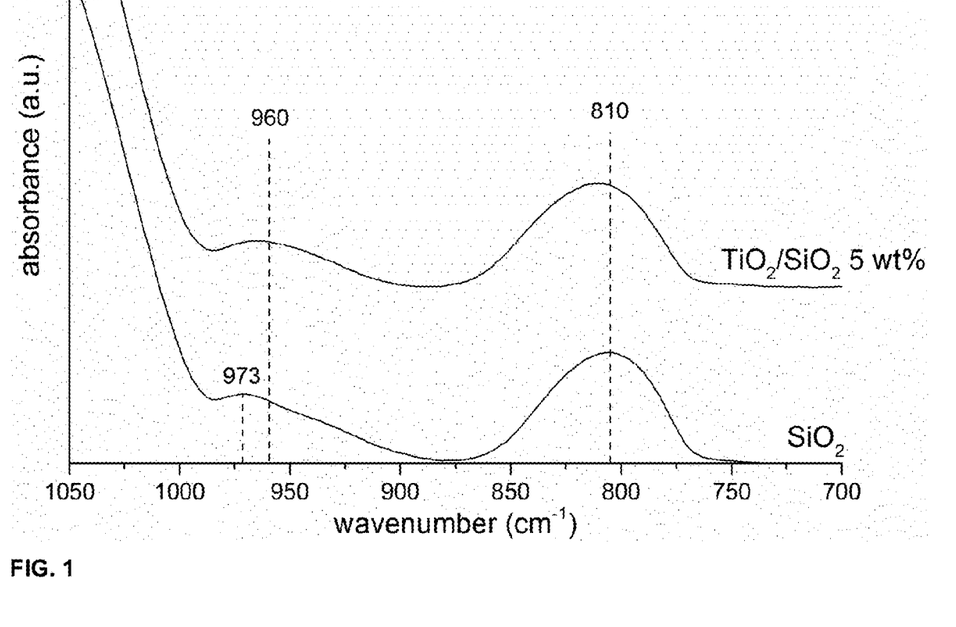
FIG. 1 FT-IR spectra of the unimpregnated $SiO_2$ support and a 5 wt % $TiO_2/SiO_2$ catalyst.

The presence of Ti—O—Si bonds between the active component (Ti) and the $SiO_2$ support was investigated by FT-IR spectroscopy and XPS. An FT-IR spectrum of the amorphous $SiO_2$ gel support exhibited a weak band at ~973 cm⁻¹ from the symmetric stretch of Si—OH groups, as well as a band at ~810 cm⁻¹ from the symmetrical Si—O—Si vibration (Gao et al., J. Phys. Chem. B. 1998, 102, 5653). The addition of titanium oxide species decreases the intensity of the 973 band with the appearance of a new broad band at ~960 cm⁻¹, indicative of Ti—O—Si bonds, see FIG. 1 (Gao et al., Catal. Today 1999, 51, 233). XPS further confirmed the presence of Ti—O—Si bonds. Binding energy (BE) values of O 1s, Ti $2p_{3/2}$ and Si 2p are presented in Table 1. Compared to the $SiO_2$ reference (entry 1), a second signal of O 1s could be resolved at ~529.8 eV for the $TiO_2/SiO_2$ catalyst. Simultaneously, a slight blue shift in BE value of Ti $2p_{3/2}$ was observed compared to $TiO_2$ (entry 3). The blue shifts observed for the BE values of both O 1s and Ti $2p_{3/2}$ with respect to pure $TiO_2$ have been associated with the presence of Ti—O—Si bonds (Gao et al., J. Phys. Chem. B. 1998, 102, 5653).

TABLE 1

| entry | material | O 1s (eV) | Ti $2p_{3/2}$ (eV) | Si 2p (eV) |
|---|---|---|---|---|
| 1 | $SiO_2$ | 532.9 | | 103.3 |
| 2 | $TiO_2/SiO_2$ 5 wt % | 532.5 (91.8%) 529.8 (8.1%) | 459.2 | 103.3 |
| 3 | $TiO_2$ | 530.5 | 458.7 | 103.3 |

Binding energy for Core Electrons

The $TiO_2/SiO_2$ catalyst was then tested for lactide production on a custom plug flow fixed-bed reactor. Different contact times were tested by varying the catalyst amount. A liquid mixture (95/5 vol %) of L-MLA (97%, Acros Organics) and o-xylene (internal standard, 99%, Acros Organics) was used as reaction feed. This feed solution was sent to a heated evaporation chamber (210° C.) by a HPLC pump, where the vapor is mixed with a $N_2$-stream to enhance full evaporation of the liquid feed. This mixed vapor stream is then sent to a reaction zone heated to 220° C., containing a quartz tube (length 480 mm, outer diameter=6 mm, inner diameter=4 mm), filled with catalyst pellets, supported by quartz wool. The catalysts pellets were diluted with quartz (150 μm particle size) to obtain a total catalyst bed weight of 300 mg. The resulting product mixture is then sent through heated transfer lines (210° C.) to a gas-chromatograph equipped with a flame ionization detector (GC/FID) for on-line analysis. The concentration of L-MLA in $N_2$ was 5.7 vol %, the reaction temperature was 220° C. and WHSV=0.5-31 $g_{MLA}\ g_{cat}^{-1}\ h^{-1}$. Samples were taken after 2 hours on stream and analysis was performed using on-line GC/FID with o-xylene as internal standard.

Figure 2:
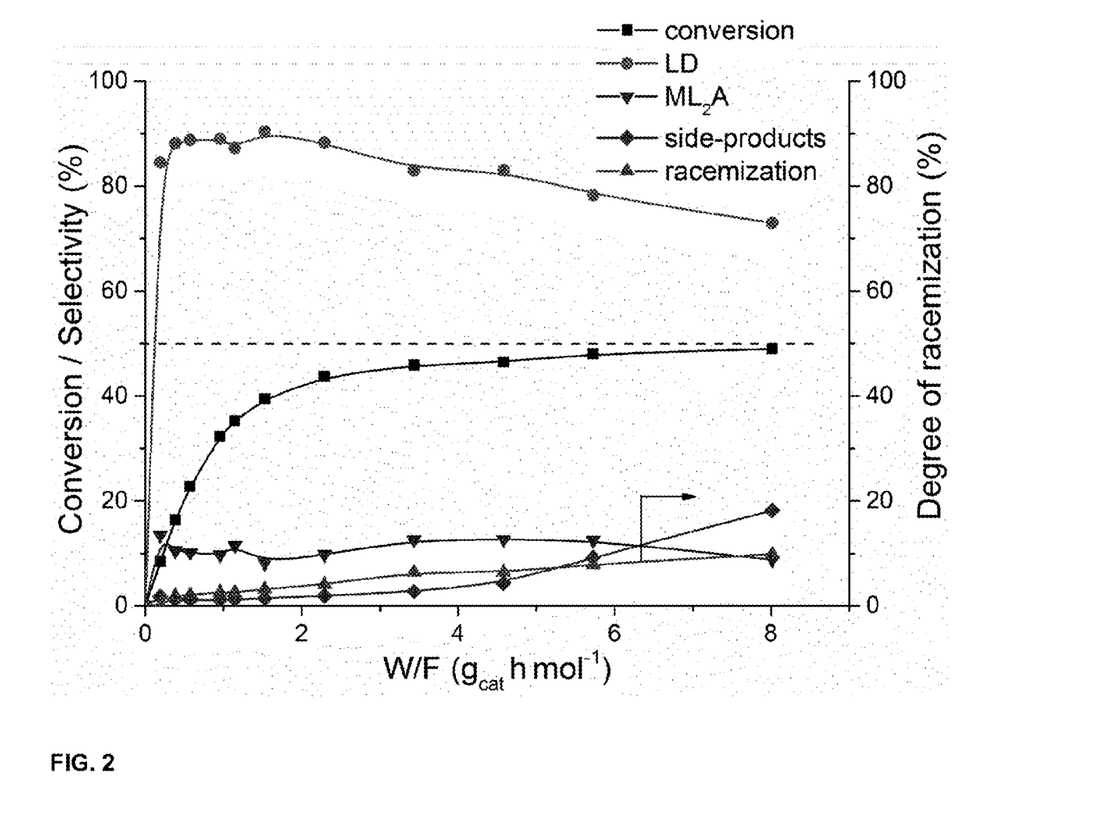
FIG. 2 Graph plotting the conversion of L-MLA and selectivity of $ML_2A$, LD, side-products and degree of racemization (% of meso-LD) at different contact times for a 5 wt % $TiO_2/SiO_2$ catalyst.

The results are given in FIG. 2. These results clearly indicate the presence of a chemical equilibrium at approximately 45-50% conversion. Below 40% conversion, LD selectivities are high, approx. 88-90%, but diminish at longer contact times due to more pronounced side reactions once chemical equilibrium is reached. Below 40% conversion, the degree of racemization is low (2-3% meso-LD).

Reference experiments were conducted using equal amounts of unimpregnated $SiO_2$ support, quartz and in the absence of a catalyst. For all reference experiments, ≤2% conversion was observed. This example demonstrates that the catalytic activity and high lactide selectivity originates from the $TiO_2$ phase that is connected to the $SiO_2$ support through Ti—O—Si bonds.

Example 2 Influence of Reaction Temperature on the Production of Lactide from Methyl Lactate In this example, we investigated the influence of reaction temperature on the production of LD from L-MLA. For this, a 5 wt % $TiO_2/SiO_2$ catalyst was tested in the same manner as in Example 1 at temperatures between 220-300° C. Reaction conditions were as follows: 5.7 vol % L-MLA in $N_2$, T=220-300° C. Samples were taken after 2 h on stream. The results are given in Table 2.

TABLE 2

| Reaction temperature (° C.) | W/F ($g_{cat}$ h mol⁻¹) | C (%) | Selectivity (%) | | side-products | % meso-LD |
|---|---|---|---|---|---|---|
| | | | LD | $ML_2A$ | | |
| 220 | 1.53 | 40 | 90 | 8 | 2 | 3 |
| 240 | 0.57 | 39 | 88 | 10 | 2 | 4 |
| 260 | 0.57 | 54 | 90 | 6 | 4 | 6 |

TABLE 2-continued

| Reaction temperature (° C.) | W/F ($g_{cat}$ h $mol^{-1}$) | C (%) | Selectivity (%) | | | % meso-LD |
| --- | --- | --- | --- | --- | --- | --- |
| | | | LD | $ML_2A$ | side-products | |
| 280 | 0.38 | 55 | 90 | 5 | 5 | 6 |
| 300 | 0.19 | 55 | 90 | 6 | 4 | 6 |

The results in Table 2 demonstrate that temperatures between 220° C. and 300° C. are suitable for producing LD from L-LMA.

Figure 3:
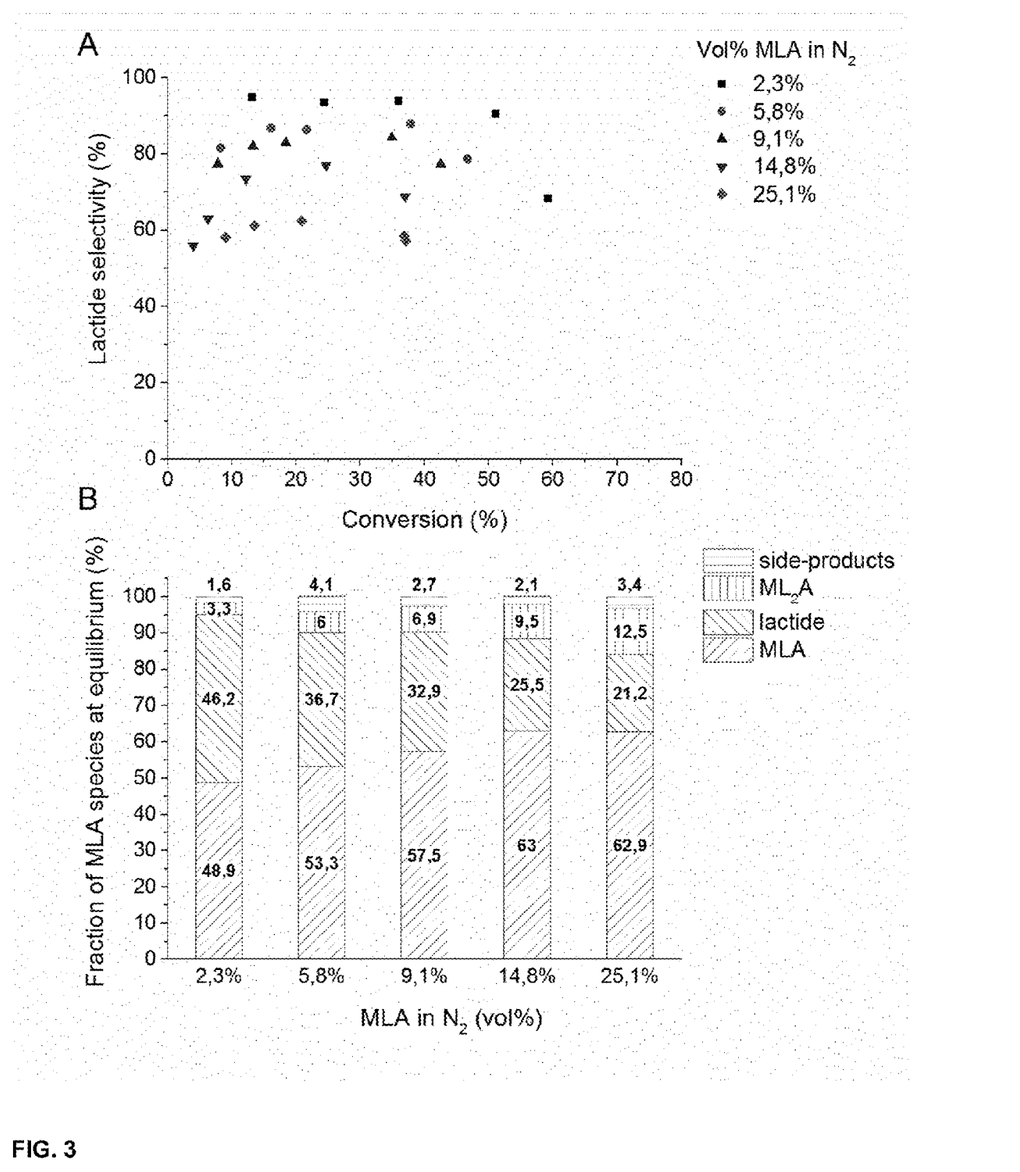

Example 3 Influence of Partial Pressure on the Production of Lactide from Methyl Lactate In this example, we demonstrate the process for making LD at different partial pressures of L-MLA. For this, a 5 wt % $TiO_2/SiO_2$ catalyst was tested in the same manner as in Example 1 at different dilutions of L-MLA in $N_2$. At increasing L-MLA content, the $N_2$ content was adjusted accordingly in order to keep the total gas flow, and thus contact time, the same. Reaction conditions were as follows: W/F=0.19-5.73 $g_{cat}$ h $mol^{-1}$, T=220° C., 2.3-25 vol % L-MLA in $N_2$. The results are given in FIGS. 3A and 3B. This example indicates that selective LD formation is possible at a range of partial pressures of L-MLA in $N_2$. Using 2.3% L-MLA in $N_2$, a 94% selectivity towards LD can be achieved. At conversions ≤50%, the amount of meso-LD was ≤5% of total LD.

Example 4 Influence of Catalyst Loading on the Production of Lactide from Methyl Lactate In this example, we demonstrate the use of $TiO_2/SiO_2$ catalysts with different weight percentages of $TiO_2$ loading, as determined by inductively coupled plasma optical emission spectroscopy (ICP-OES). For this, different $TiO_2/SiO_2$ catalysts were tested in the same manner as in Example 1. Reaction conditions were as follows: T=220° C., 5.7 vol % L-MLA in $N_2$. The results are given in Table 3. This example demonstrates that different $TiO_2$ loadings can be used for the selective (≥80%) production of LD from L-MLA.

TABLE 3

| $TiO_2$ loading of $TiO_2/SiO_2$ (wt %) | W/F ($g_{cat}$ h $mol^{-1}$) | C (%) | Selectivity (%) | | | % meso-LD |
| --- | --- | --- | --- | --- | --- | --- |
| | | | LD | $ML_2A$ | side-products | |
| 0.4 | 1.52 | 14 | 91 | 8 | 1 | 2 |
| 1.1 | 5.73 | 43 | 91 | 8 | 1 | 3 |
| 4.7 | 1.53 | 38 | 88 | 10 | 2 | 4 |
| 10.4 | 1.53 | 43 | 89 | 8 | 3 | 5 |
| 20.1 | 1.53 | 36 | 87 | 9 | 4 | 5 |
| 30.4 | 0.38 | 11 | 83 | 12 | 5 | 1 |

Example 5 Production of Lactide from Methyl Lactate with a $ZrO_2/SiO_2$ Catalyst In this example, we demonstrate the selective production of lactide from L-MLA using a $ZrO_2/SiO_2$ catalyst (5 wt % $ZrO_2$ loading) containing Zr—O—Si bonds between the active phase ($ZrO_2$) and the $SiO_2$ support. The catalyst was prepared in the same manner as in Example 1, but in this case, the metal precursor was $ZrO(NO_3)_2 \cdot xH_2O$ and the solvent was water. The catalyst was then tested in the same manner as in Example 1. The reaction conditions were as follows: 5.7% L-MLA in $N_2$, T=220° C., W/F=5.7 $g_{cat}$ h $mol^{-1}$. After 2 hours on stream, the conversion of L-MLA was 43%, selectivities of LD and $ML_2A$ were 86% and 14% respectively. No side products were detected. The percentage of meso-LD was 22% of total LD. This example demonstrates that $ZrO_2/SiO_2$, containing Zr—O—Si bonds can produce LD directly from L-MLA at high selectivity, but that % of meso-LD is significantly higher than for $TiO_2/SiO_2$ catalysts.

Example 6 Long-Term Stability of $TiO_2/SiO_2$ and $ZrO_2/SiO_2$ in the Production of Lactide from Methyl Lactate In this example, the process is run for longer times at steady state, to assess the stability of the catalytic system during the production of LD from MLA with $TiO_2/SiO_2$ and $ZrO_2/SiO_2$. For this, the 5 wt % $TiO_2/SiO_2$ catalyst from Examples 1-3 and the 5 wt % $ZrO_2/SiO_2$ catalyst from example 5 were tested in the same manner as in Example 1. Reaction conditions were as follows: 5.7 vol % L-MLA in $N_2$, WHSV=2.6 $h^{-1}$, T=220° C. The reaction was left to proceed for 50 h. GC analysis of the product stream showed that for 5 wt % $TiO_2/SiO_2$, conversion of L-MLA after 1 hour was 47%, while selectivities of LD and of $ML_2A$ were 87 and 10% respectively. The percentage of meso-LD was 5% of total LD. After 50 hours, conversion of L-MLA was 43% and selectivities of LD and $ML_2A$ were 90 and 8% respectively. The percentage of meso-LD was 4% of total LD. This catalytic system still works after prolonged action. For 5 wt % $ZrO_2/SiO_2$, conversion of L-MLA after 1 hour was 38%, selectivities of LD and $ML_2A$ were 87 and 13% respectively. The percentage of meso-LD was 14% of total LD. After 50 hours, conversion of L-MLA was 27%, selectivity of LD and $ML_2A$ was 87 and 12% respectively. The percentage of meso-LD was 10% of total LD. This catalytic system still works after prolonged action but lost a fraction of its initial activity.

Example 7 Production of Lactide from Methyl Lactate with a $SnO_2/SiO_2$ Catalyst In this example, we tested the production of LD from L-MLA with a $SnO_2/SiO_2$ catalyst (10 wt % $SnO_2$ loading). The catalyst was prepared in the same manner as in Example 1, but in this case, the metal precursor was $SnCl_{4.5}H_2O$ and the solvent was isopropanol. The catalyst was then tested in the same manner as in Example 1. The reaction conditions were as follows: 5.7% L-MLA in $N_2$, T=220° C., WHSV=1.04 $h^{-1}$. After 20 minutes on stream, the conversion of L-MLA was 32%, selectivities of LD and $ML_2A$ were 88% and 11% respectively. The percentage of meso-LD was 6% of total LD. After 3 hours on stream, the conversion of L-MLA decreased to 12%, with no changes in product selectivity. This example demonstrates that $SnO_2/SiO_2$ catalysts are not preferred for lactide production from L-MLA due to rapid deactivation.

Example 8 Production of Lactide from Methyl Lactate with a $TiO_2$—$SiO_2$ Gel Catalyst In this example, we demonstrate the use of a $TiO_2$—$SiO_2$ gel catalyst, prepared through a sol-gel synthesis procedure. For this, tetraethylorthosilicate (TEOS), diluted with ethanol (mol EtOH:TEOS=2) was mixed with an aqueous 0.05 M HCl solution (mol $H_2O$:TEOS=1.2) and was stirred at room temperature for 90 minutes. Then, the solution was cooled in an ice bath and Ti(iOPr)$_4$, diluted 1:1 in isopropanol, was added dropwise. The resulting solution was stirred for 45 minutes and then, extra $H_2O$ was added so that the molar ratio of $H_2O$/(TEOS+Ti(iOPr)$_4$)=4. After stirring for another 60 minutes, a 1M $NH_3$ solution was added dropwise to the sol, until gelation occurred. This results in a $TiO_2$—$SiO_2$ gel wherein $TiO_2$ is distributed homogeneously within the $SiO_2$ matrix. The resulting gel was let to ripe at room temperature for 24 hours, dried overnight at 80° C. and afterwards calcined at 500° C. for 4 hours (heating rate 5° C. min$^{-1}$) to obtain the final catalyst. The amount of $TiO_2$ according to ICP was 4 wt %. The presence of Ti—O—Si bonds was confirmed by FT-IR and XPS in an analogue manner as in Example 1 (Gao et al., Catalysis Today, 1999, 51, 233). The resulting catalyst was tested in the same manner as Example 1. Reaction conditions were as follows: 5.7 vol % L-MLA in $N_2$, WHSV=2.6 h$^{-1}$, T=220° C. The conversion of L-MLA after 1 hour was 44%, selectivities of LD and $ML_2A$ were 88% and 11% respectively. The percentage of meso-LD was 4% of total LD.

Example 9 Production of Lactide from Methyl Lactate with Ti-Zeolites

In this example two Ti-zeolites, viz. Ti-beta and TS-1, containing the BEA and MFI topology respectively (Database of Zeolite Structures: http://www.iza-structure.org/databases/), were tested for the production of LD from L-MLA. Ti-beta was synthesized according to a procedure proposed by Blasco et al. (Blasco et al., Chemical Communications, 1996, 3, 2367). TS-1 was synthesized in OH$^-$ medium according to Carati et al. (Carati et al., Studies in Surface Science and Catalysis, vol 125, 1999, p 45-52). The BEA topology contains 12-membered straight channels (6.6-6.7 Å) interconnected by 12-membered zigzag channels (5.6 Å). The MFI topology comprises 10-membered rings with straight channels (5.5-6 Å) interconnected by sinusoidal channels. Both zeolite types contain isolated Ti atoms coordinated tetrahedrally in the crystalline $SiO_2$ framework through Ti—O—Si bonds, as confirmed by DR UV-VIS and FT-IR spectroscopy. (Boccuti et al. (1989), Spectroscopic Characterization of Silicalite and Titanium-silicatite, G. Costa et al. (Eds.), in *Structure and Reactivity of Surfaces* (pp 133-144), Amsterdam, Elsevier Science Publishers B.V.) Reaction conditions were as follows: 5.7 vol % L-MLA in $N_2$, WHSV=7.8 h$^{-1}$, T=220° C. The results are summarized in Table 4.

TABLE 4

| Catalyst | $TiO_2$ (wt %) | C (%) | Selectivity (%) | | | |
|---|---|---|---|---|---|---|
| | | | LD | $ML_2A$ | side-products | % meso-LD |
| Ti-beta | 0.4 | 21 | 74 | 10 | 16 | 2 |
| TS-1 | 2.85 | 24 | 88 | 9 | 3 | 2 |

Example 10 Production of Lactide with a $TiO_2$/MCM-41 Catalyst

For this example, a Si-MCM-41 support was prepared by dissolving 14.6 g of cetyl trimethylammonium bromide in 271 g of water and stirring the mixture for 15 minutes. Then, 356 g of ethanol was added, followed by 99.7 g of a 25 wt % aqueous solution of $NH_3$. This mixture was stirred for another 15 minutes and afterwards, 27.8 g of tetraethylorthosilicate was added, after which the mixture was left for 2 hours under continuous stirring. The resulting powder was filtered, washed with ethanol and water, dried at 80° C. overnight and subsequently calcined at 550° C. for 8 hours (heating rate: 1° C. min$^{-1}$). The resulting Si-MCM-41 had a uniform pore width of 2.2 nm, a $S_{BET}$ of 926 m$^2$ g$^{-1}$ and a pore volume of 0.582 cm$^3$ according to $N_2$ physisorption analysis. The Si-MCM-41 support was then impregnated with different mixtures of Ti-isopropoxide in isopropanol by incipient wetness impregnation, as described in Example 1, in order to obtain different weight loadings of $TiO_2$ (determined by ICP-OES) supported on MCM-41 ($TiO_2$/MCM-41). The impregnated catalysts were dried overnight at 80° C. and calcined again at 500° C. for 4 hours (heating rate: 5° C. min$^{-1}$). The presence of Ti—O—Si bonds was confirmed by FT-IR and XPS in an analogue manner as in Example 1. The final catalysts were tested in the same manner as in Example 1 for the production of LD from L-MLA. Reaction conditions were as follows: 5.7% L-MLA in $N_2$, T=220° C. Samples were taken after 2 hours on stream, the results are summarized in Table 5. This example demonstrates that the $SiO_2$ support may have an ordered mesoporous structure.

TABLE 5

| $TiO_2$ loading of $TiO_2$/ MCM-41 (wt %) | W/F ($g_{cat}$ h mol$^{-1}$) | C (%) | Selectivity (%) | | | |
|---|---|---|---|---|---|---|
| | | | LD | $ML_2A$ | side-products | % meso-LD |
| 0.1 | 3.81 | 17 | 91 | 7 | 1 | 3 |
| 0.8 | 0.57 | 28 | 90 | 9 | 1 | 2 |
| 4.2 | 0.38 | 29 | 91 | 8 | 1 | 2 |
| 8.4 | 0.38 | 32 | 90 | 9 | 1 | 3 |
| 16.9 | 0.38 | 27 | 90 | 9 | 1 | 4 |

Example 11 Production of Lactide from Ethyl Lactate

A 5 wt % $TiO_2$/$SiO_2$ was tested in the same manner as in Example 1 for the production of LD from L-ethyl lactate (L-ELA). Reaction conditions were as follows: 4.6 vol % L-ELA in $N_2$, WHSV=3.7 h$^{-1}$, T=220° C. Samples were taken after 2 hours on stream. GC analysis of the product stream showed that conversion of L-ELA was 40%, selectivities of LD and of the linear dimer ($EL_2A$) were 87 and 11% respectively. The percentage of meso-LD was 4% of total LD. Ethyl lactates are thus also very suitable ester feedstocks for the process.

Example 12 Production of Lactide from Butyl Lactate

A 5 wt % $TiO_2$/$SiO_2$ was tested in the same manner as in Example 1 for the production of LD from L-n-butyl lactate (L-BLA). Reaction conditions were as follows: 5.8 vol % L-BLA in $N_2$, WHSV=15.0 h$^{-1}$, T=220° C. Samples were taken after 2 hours on stream. GC analysis of the product stream showed that conversion of L-BLA was 20%, selectivity of LD and of the linear dimer ($EL_2A$) was 80 and 13% respectively. The percentage meso-LD was 3% of total LD. Butyl lactates are thus also very suitable ester feedstocks for the process.

Example 13 Production of Glycolide from Methyl Glycolate with a $TiO_2$/$SiO_2$ Catalyst In this example, we demonstrate the selective production of glycolide from methyl glycolate using the same $TiO_2$/

$SiO_2$ 5 wt % catalyst from Example 1 and in the same manner as in Example 1. The feed solution consisted of 95/5 vol % of methyl glycolate (>98%, TCI Europe) and o-xylene respectively. The reaction conditions were as follows: 5.6 vol % methyl glycolate in $N_2$, T=300° C., WHSV=8.8 $h^{-1}$. After 2 hours on stream, methyl glycolate conversion was 52% and selectivity to glycolide was 77%. The selectivity towards linear dimers and trimers was 8 and 15% respectively.

Figure 4:
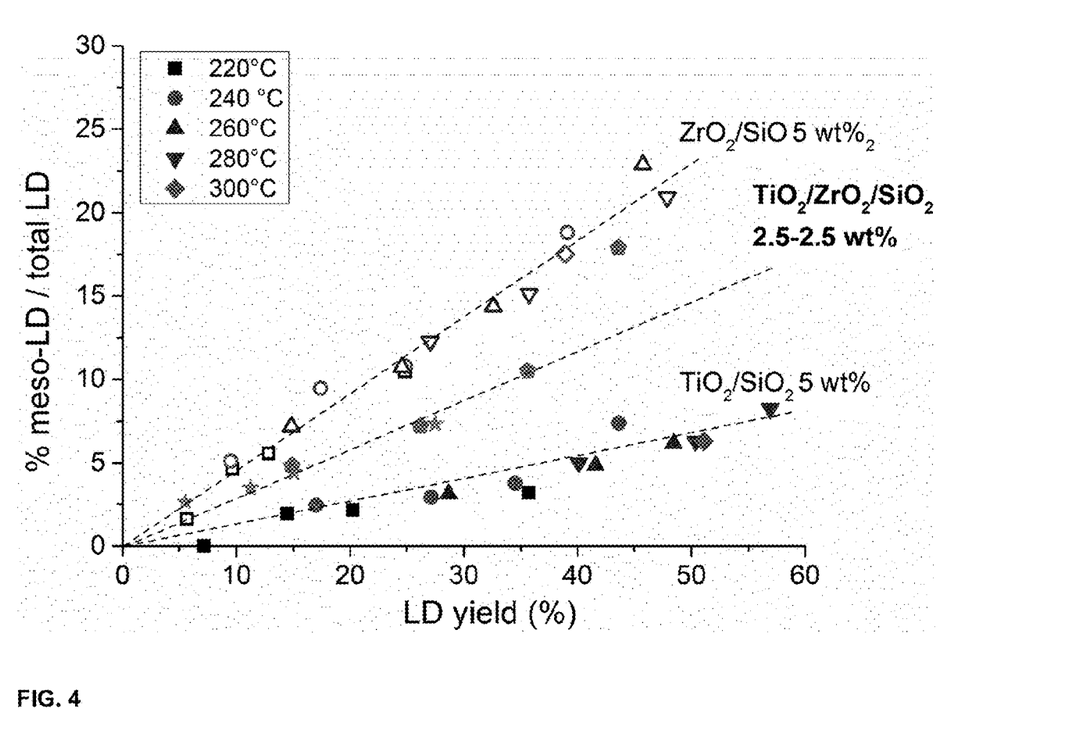
FIG. 4 Percentage of meso-LD in the product stream at different LD yields for a 5 wt % $TiO_2/SiO_2$ catalyst, a 5 wt % $ZrO_2/SiO_2$ catalyst and a bifunctional $TiO_2$—$ZrO_2/SiO_2$ catalyst (2.5 wt % $TiO_2$ and 2.5 wt % $ZrO_2$).

Example 14 Controlled Racemization of Lactide with Bifunctional $TiO_2$—$ZrO_2/SiO_2$ Catalyst In this example, we demonstrate that the racemization of the lactide product can be controlled by a bifunctional catalyst containing both $ZrO_2$ and $TiO_2$, wherein Ti and Zr are connected to the $SiO_2$ support by Ti—O—Si and Zr—O—Si bonds respectively. For this, a bifunctional $TiO_2$—$ZrO_2/SiO_2$ catalyst (2.5 wt % $TiO_2$, 2.5 wt % $ZrO_2$) was prepared. First, a $ZrO_2/SiO_2$ (2.5 wt % $ZrO_2$) catalyst was prepared in the same manner as Example 5. Afterwards, the same catalyst was impregnated by Ti-isopropoxide diluted in isopropanol, dried and calcined as described in Example 1 to obtain the bifunctional $TiO_2$—$ZrO_2/SiO_2$ catalyst. The catalyst was then tested for the production of lactide from L-MLA in the same manner as in Example 1. Reaction conditions were as follows: 5.7% L-MLA in $N_2$, T=220-300° C., WHSV=3.88-31.07 $h^{-1}$. The bifunctional $TiO_2$—$ZrO_2/SiO_2$ catalyst (2.5 wt % $TiO_2$, 2.5 wt % $ZrO_2$) was compared to the $TiO_2/SiO_2$ (5 wt % $TiO_2$) and $ZrO_2/SiO_2$ (5 wt % $ZrO_2$) catalysts from Example 1 and 5 respectively. The results are shown in FIG. 4. Clearly, the % of meso-LD in the product stream depends on the lactide yield and on the catalyst. For the $TiO_2/SiO_2$ catalyst, the % of meso-LD was ≤7% for LD yields ≤60%. For the $ZrO_2/SiO_2$ catalyst, the % of meso-LD was much higher at all LD yields, viz. ≤25% for LD yields ≤50%. For the bifunctional $TiO_2$—$ZrO_2/SiO_2$, the % of meso-LD was intermediate to that of $TiO_2/SiO_2$ and $ZrO_2/SiO_2$. This example demonstrates that the % of meso-LD in the product stream can be controlled by tuning the amount of $TiO_2$ and $ZrO_2$ on the catalyst.

Comparative Example 1 Production of Lactide from Methyl Lactate with Bulk $TiO_2$ Different commercial $TiO_2$ powders, containing different crystal structures and not having any Ti—O—Si bonds with a $SiO_2$ support, were tested for the production of LD from MLA. For this, the catalysts were crushed and sieved to uniform pellets of 250-500 µm. The catalysts were tested in the same manner as Example 1. Reaction conditions were as follows: 5.7 vol % L-MLA in $N_2$, WHSV=2.59 $h^{-1}$, T=220° C. Samples were taken after 2 h on stream. The results are summarized in Table 6. TP Hombikat M211-411 were provided by Sachtleben.

TABLE 6

| Catalyst | Crystal structure of $TiO_2$ | C (%) | Selectivity (%) LD | Selectivity (%) $ML_2A$ | Selectivity (%) side-products | % meso-LD |
|---|---|---|---|---|---|---|
| TP Hombikat M211 | anatase | 32 | 11 | 4 | 85 | 16 |
| TP Hombikat M311 | anatase | 39 | 11 | 5 | 84 | 18 |
| TP Hombikat M411 | anatase | 31 | 21 | 6 | 73 | 14 |
| $TiO_2$ rutile | rutile | 6 | 0 | 0 | 100 | — |
| Degussa P25 | 75% anatase 25% rutile | 17 | 0 | 0 | 100 | — |

Detected side products include acetaldehyde, methyl acrylate, 2,3-pentanedione, methyl pyruvate and methyl-2-methoxy-propionate. As can be seen, pure $TiO_2$ catalysts not having any Ti—O—Si bonds with a $SiO_2$ support are not able to selectively produce LD from MLA.

Comparative Example 2 Production of Lactide from Methyl Lactate with a Physical Mixture of $TiO_2$ and $SiO_2$ Support Different commercial $TiO_2$ powders, containing different crystal structures, were physically mixed with a non-impregnated $SiO_2$ support and tested for the production of LD from L-MLA. This way, physical mixtures of $TiO_2$ and $SiO_2$, containing 5 wt % of $TiO_2$, were obtained, that do not have Ti—O—Si bonds between the $TiO_2$ and $SiO_2$ support. The mixed powders were then crushed and sieved into uniform pellets of 250-500 µm. The catalysts were tested in the same method as Example 1. Reaction conditions were as follows: 5.7 vol % L-MLA in $N_2$, WHSV=2.59 $h^{-1}$ T=220° C. Samples were taken after 2 h on stream. The results are summarized in Table 7. TP Hombikat M211-411 were provided by Sachtleben.

TABLE 7

| Catalyst (physical mixture, 5-95 wt/wt $TiO_2$—$SiO_2$) | Crystal structure of $TiO_2$ | C (%) | Selectivity (%) LD | Selectivity (%) $ML_2A$ | Selectivity (%) side-products | % meso-LD |
|---|---|---|---|---|---|---|
| TP Hombikat M211-$SiO_2$ | anatase | 2 | 0 | 0 | 100 | 0 |
| TP Hombikat M311-$SiO_2$ | anatase | 3 | 0 | 0 | 100 | 0 |
| TP Hombikat M411-$SiO_2$ | anatase | 3 | 0 | 0 | 100 | 0 |
| $TiO_2$ rutile-$SiO_2$ | rutile | 2 | 0 | 0 | 100 | 0 |
| Degussa P25-$SiO_2$ | 75% anatase 25% rutile | 2 | 0 | 0 | 100 | 0 |

Comparative examples 1 and 2 show that in the absence of Ti—O—Si bonds, $TiO_2$ based catalysts are far less active and far less selective towards lactide. Compared to Examples 1 to 12, this demonstrates the necessity of M-O—Si bonds to obtain a high selectivity towards the cyclic ester. As can be seen, physical mixtures of $TiO_2$ and $SiO_2$, without the Ti—O—Si bonds, do not work as catalysts in the process of the present invention.

Comparative Example 3 Production of Lactide from Methyl Lactate with Bulk Oxides Other than $TiO_2$ In this example, different commercial metal oxides other than $TiO_2$, and which did not have any M-O—Si bonds, were tested for the production of LD from L-MLA. The catalysts were tested in the same method as Example 1. Reaction conditions were as follows: 5.7 vol % L-MLA in $N_2$, WHSV=1.04 $h^{-1}$, T=220° C. Samples were taken after 2 h on stream. The results are summarized in Table 8.

TABLE 8

| Metal oxide | C (%) | Selectivity (%) | | | % meso-LD |
| --- | --- | --- | --- | --- | --- |
| | | LD | $ML_2A$ | side-products | |
| $La_2O_3$ | 12 | 62 | 37 | 1 | 18 |
| $Sn^{II}O_2$ | 6 | 56 | 43 | 1 | 1 |
| $Sn^{IV}O_2$ | 4 | 0 | 0 | 100 | — |
| $ZrO_2$ | 7 | 51 | 43 | 6 | 1 |
| $\gamma$-$Al_2O_3$ | 11 | 70 | 14 | 16 | 14 |
| $\alpha$-$Al_2O_3$ | 0 | — | — | — | — |

This example shows that pure metal oxides, lacking M—O—Si bonds have a very low activity towards MLA conversion with only mediocre selectivity to LD.

Comparative Example 4 Production of Lactide from Methyl Lactate with a $SnO_2(80)/SiO_2$ Catalyst In this example, we demonstrate that a $SnO_2(80)/SiO_2$ nanocomposite catalyst, which has been reported to be active for lactide production by lactic acid condensation (U.S. Pat. No. 9,539,561 B2), is not active for the transesterification of methyl lactate in the gas-phase. The $SnO_2(80/SiO_2$ catalyst was prepared according to the procedure reported in U.S. Pat. No. 9,539,561 B2. The catalyst was then tested in the same manner as in Example 1. The reaction conditions were as follows: 5.7% L-MLA in $N_2$, T=220° C., WHSV=2.59 $h^{-1}$. After 2 hours on stream, the conversion of L-MLA was only 2%. This example demonstrates that a $SnO_2(80/SiO_2$ nanocomposite catalyst, reported to be active for lactic acid condensation to lactide, is not active for the gas-phase transesterification of MLA to LD.

Present invention concerns a process for preparing at least one cyclic ester by a catalyzed gas phase transesterification reaction of at least one alpha-hydroxy ester, characterized in that a) the solid catalyst comprises at least one metal (M) of Titanium (Ti) and Zirconium (Zr), this metal being chemically bound to a support through a metal-oxygen-silicon (M—O—Si) chemical bond and b) the process comprises (i) vaporizing at least one alpha-hydroxy ester into a gas phase of ester vapor or comprising ester vapor; (ii) passing the gas phase over said solid catalyst and (iii) recovering the cyclic esters from this gaseous product stream. A particular aspect of the invention is that metal-oxygen-silicon chemical bond is a covalent bond and that the support comprises silicon dioxide ($SiO_2$). Moreover the metal can be on the surface of the support, it can be incorporated within the bulk framework of the support and/or it can be incorporated within the crystalline framework of a zeolite. According to the present invention there is also provided that the catalyst comprises titanium (Ti) bound to the support through titanium-oxygen-silicon (Ti—O—Si) chemical bonds or wherein the catalyst comprises titanium chemically bound to silicon (Si) through oxygen or that the catalyst comprises zirconium (Zr) bound to the support through zirconium-oxygen-silicon (Zr—O—Si) chemical bonds or wherein the catalyst comprises zirconium chemically bound to silicon (Si) through oxygen. In this process the cyclic ester can be a compound of formula (1):

wherein R1, R2, R3 and R4 are each independently selected from hydrogen or a group selected from C1-6alkyl; C2-6 alkenyl; C6-10aryl, C1-10alkylC6-10arylene; C6-10arylC1-6alkylene; or C2-6 alkynyl; each group optionally substituted by one or more substituents selected from C1-6alkyl, C1-6alkoxy or the cyclic ester can be a compound of formula (2):

wherein R1 and R2 are each independently selected from hydrogen or a group selected from C1-6alkyl; C2-6 alkenyl; C6-10aryl, C1-10alkylC6-10arylene; C6-10arylC1-6alkylene; or C2-6 alkynyl; each group optionally substituted by one or more substituents selected from C1-6alkyl, C1-6alkoxy, moreover the alpha-hydroxy ester can be selected from the group consisting of $C_{1-6}$alkyl esters of lactic acid, glycolic acid, 2-hydroxy butyric acid, 2-hydroxy-3-butenoic acid, 4-methoxy-2-hydroxy butanoic acid and mandelic acid or mixtures thereof or the cyclic ester is lactide and said alpha-hydroxy ester is a $C_{1-6}$alkyl ester of lactic acid or mixtures thereof.

The present invention provides also that the cyclic ester is lactide and said alpha-hydroxy ester is methyl lactate, ethyl lactate, n-propyl lactate, n-butyl lactate or structural isomers thereof, or that the cyclic ester is L,L-lactide and said alpha-hydroxy ester is L-methyl lactate, L-ethyl lactate, L-propyl lactate or L-butyl lactate or that the cyclic ester is D,D-lactide and said alpha-hydroxy ester is D-methyl lactate, D-ethyl lactate, D-propyl lactate or D-butyl lactate or that the cyclic ester is a mixture of L,L-lactide; L,D-lactide and D,D-lactide and said alpha-hydroxy ester is a mixture of both L- and D-methyl lactate, L- and D-ethyl lactate, L- and D-propyl lactate or L- and D-butyl lactate or that the cyclic ester comprises a mixture of L,L-lactide; L,D-lactide and D,D-lactide and said alpha-hydroxy ester is L-methyl lactate, L-ethyl lactate, L-propyl lactate or L-butyl lactate; and wherein at least one metal of the catalyst catalyzes the isomerization of L,L-lactide to D,L-lactide and D,D-Lactide or that the cyclic ester comprises a mixture of L,L-lactide; L,D-lactide and D,D-lactide and said alpha-hydroxy ester is D-methyl lactate, D-ethyl lactate, D-propyl lactate or D-butyl lactate; and wherein at least one metal of the catalyst catalyzes the isomerization of D,D-lactide to L,D-lactide and L,L-lactide. Optimal processes as described above are obtained when the phase comprises an inert gas, such as N2. Moreover the catalyst is preferably contained in a reaction zone at a temperature of a value between 200 and 300° C. or wherein the catalyzed gas phase transesterification is performed at a temperature of a value between 200 and 300° C. and the catalyzed gas phase transesterification is preferably performed at a pressure between 0.1 and 20 bar, preferably between 0.8 and 1.2 bar.

This embodiment of the invention advantageously comprises at least one metal of titanium (Ti) and zirconium (Zr) in an amount of a value between 0.05 and 30% by weight of the catalyst, preferably between 0.5 and 10% by weight of the catalyst.

A further disadvantageous aspect of present invention is also, that the processes according to any of the previous embodiments can be used to control degree of racemization of L,L- or D,D-lactide to meso-lactide (L,D- or D,L-lactide) by varying the ratio of Ti and Zr, which are bound to the support by metal-oxygen-silicon (M-O—Si) bonds between the metal and the support. For instance in a process according to the present invention that is characterised in that said alpha-hydroxy ester is L-methyl lactate and M is titanium (Ti), bound to the support by titanium-oxygen-silicon (Ti—O—Si) chemical bonds, this process produces L,L-lactide with yields of 40 to 50%. While in a process according to the present invention that is characterised in that said alpha-hydroxy ester is L-methyl lactate and M is titanium (Ti), bound to the support by titanium-oxygen-silicon (Ti—O—Si) chemical bonds, L,L-lactide, will be produced that comprises ≤7% meso-lactide (L,D- or D,L-lactide). And in such a process characterised in that said alpha-hydroxy ester is L-methyl lactate and M is zirconium (Zr), bound to the support by zirconium-oxygen-silicon (Zr—O—Si) chemical bonds, so that said process manufactures L,L-lactide, the lactide product produced will comprise ≤30% meso-lactide (L,D- or D,L-lactide). While in such process according to present invention that is characterised in that said alpha-hydroxy ester is L-methyl lactate and M is a mixture of titanium (Ti) and zirconium (Zr), bound to the support by metal-oxygen-silicon (M-O—Si) chemical bonds, and wherein the isomerization of lactide is proportional to the ratio of Ti and Zr, it manufactures L,L-lactide wherein the lactide product comprises ≥7 but ≤30% meso-LD.

In a practical embodiment, the liquid ester fed into the gas phase is a pure solution of ≥95% of only one type of alpha-hydroxy ester or the liquid ester fed into the gas phase is completely free of or comprise less than 1 percent by weight, such as less than 0.05 percent by weight, of lactic acid or the liquid ester fed into the gas phase is substantially free of lactic acid or the liquid ester fed into the gas phase is a pure isomeric form of an alpha-hydroxy ester or the liquid ester fed into the gas phase is substantially free of hydroxyl acids.

LEGEND TO THE GRAPHICS OF THE APPLICATION

The following description of the figures of specific embodiments of the invention is merely exemplary in nature and is not intended to limit the present teachings, their application or uses.

FIG. 3 A: Graph plotting the selectivity of LD in function of L-MLA conversion for different dilutions of L-MLA in $N_2$. B: Graph plotting the distribution of MLA species at kinetic equilibrium for different dilutions of L-MLA in $N_2$.

The invention claimed is:

1. A process for preparing at least one cyclic ester of formula (1):

wherein R1, R2, R3 and R4 are each independently selected from hydrogen or a group selected from C1-6alkyl; C2-6alkenyl;
C6-10aryl, C1-10alkylC6-10arylene; C6-10arylC1-6alkylene; or
C2-6alkynyl;
each group optionally substituted by one or more substituents selected from C1-6alkyl, C1-6alkoxy, by a catalyzed gas phase transesterification reaction of at least one alpha-hydroxy ester,
wherein a) a solid catalyst comprises Titanium (Ti) chemically bound to Silicon (Si) through Oxygen, and b) the process comprises
(i) vaporizing at least one alpha-hydroxy ester selected from the group consisting of $C_{1-6}$alkyl esters of lactic acid, glycolic acid, 2-hydroxy butyric acid, 2-hydroxy-3-butenoic acid, 4-methoxy-2-hydroxy butanoic acid and mandelic acid or mixtures thereof into a gas phase of ester vapor or comprising ester vapor;
(ii) passing the gas phase over said solid catalyst and (iii) recovering the cyclic esters from this gaseous product stream.

2. The process according to claim 1, wherein said cyclic ester is a compound of formula (2):

wherein R1 and R2 are each independently selected from hydrogen or a group selected from C1-6alkyl;
C2-6alkenyl;
C6-10aryl, C1-10alkylC6-10arylene;
C6-10arylC1-6alkylene; or C2-6alkynyl;
each group optionally substituted by one or more substituents selected from C1-6alkyl, C1-6alkoxy.

3. The process according to claim 1, wherein said cyclic ester is lactide and said alpha-hydroxy ester is a $C_{1-6}$alkyl ester of lactic acid or mixtures thereof.

4. The process according to claim 1, wherein said cyclic ester is lactide and said alpha-hydroxy ester is methyl lactate, ethyl lactate, n-propyl lactate, n-butyl lactate.

5. The process according to claim 1, wherein the support comprises silicon dioxide (SiO2).

6. The process according to claim 1, wherein the metal is on the surface of the support.

7. The process according to claim 1, wherein the metal is incorporated within the bulk framework of the support.

8. The process according to claim 1, wherein the metal is incorporated within the crystalline framework of a zeolite.

9. The process according to claim 1, wherein said cyclic ester is L,L-lactide and said alpha-hydroxy ester is L-methyl lactate, L-ethyl lactate, L-propyl lactate or L-butyl lactate.

10. The process according to claim 1, wherein said cyclic ester is D,D-lactide and said alpha-hydroxy ester is D-methyl lactate, D-ethyl lactate, D-propyl lactate or D-butyl lactate.

11. The process according to claim 1, wherein said cyclic ester is a mixture of L,L-lactide;
L,D-lactide and D,D-lactide and said alpha-hydroxy ester is a mixture of both L- and D-methyl lactate, L- and D-ethyl lactate, L- and D-propyl lactate or L- and D-butyl lactate.

12. The process according to claim 1, wherein said cyclic ester comprises a mixture of L,L-lactide;
L,D-lactide and D,D-lactide and said alpha-hydroxy ester is L-methyl lactate, L-ethyl lactate, L-propyl lactate or L-butyl lactate; and
wherein at least one metal of the catalyst catalyzes the isomerization of L,L-lactide to D,L-lactide and D,D-lactide.

13. The process according to claim 1, wherein said cyclic ester comprises a mixture of L,L-lactide;
L,D-lactide and D,D-lactide and said alpha-hydroxy ester is D-methyl lactate, D-ethyl lactate, D-propyl lactate or D-butyl lactate; and
wherein at least one metal of the catalyst catalyzes the isomerization of D,D-lactide to L,D-lactide and L,L-lactide.

14. The process according to claim 1, wherein the gas phase comprises an inert gas.

15. The process according to claim 14, wherein said inert gas is N2.

16. The process according to claim 1, wherein the catalyst is contained in a reaction zone at a temperature of a value between 200 and 300° C.

17. The process according to claim 1, wherein the catalyzed gas phase transesterification is performed at a pressure between 0.1 and 20 bar.

18. The process according to claim 1, wherein the catalyst comprises at least one metal of titanium (Ti) and zirconium (Zr) in an amount of a value between 0.05 and 30% by weight of the catalyst.

19. The process according to claim 1, wherein said alpha-hydroxy ester is L-methyl lactate and M is titanium (Ti), bound to the support by titanium-oxygen-silicon (Ti—O—Si) chemical bonds, so that said process produces L,L-lactide with yields of 40 to 50%.

20. The process according to claim 1, wherein said alpha-hydroxy ester is L-methyl lactate and M is titanium (Ti), bound to the support by titanium-oxygen-silicon (Ti—O—Si) chemical bonds, so that said process manufactures L,L-lactide, and wherein the lactide product comprises ≤7% meso-lactide (L,D- or D,L-lactide).

21. The process according to claim 1, whereby the liquid ester fed into the gas phase is a pure solution of ≥95% of only one type of alpha-hydroxy ester.

22. The process according to claim 1, whereby the liquid ester fed into the gas phase is completely free of or comprises less than 1 percent by weight of lactic acid.

23. The process according to claim 1, whereby the liquid ester fed into the gas phase is free of lactic acid.

24. The process according to claim 1, whereby the liquid ester fed into the gas phase is a pure isomeric form of an alpha-hydroxy ester.

25. The process according to claim 1, whereby the liquid ester fed into the gas phase is free of hydroxyl acids.

26. The process according to claim 1, wherein the catalyzed gas phase transesterification is performed at a temperature of a value between 200 and 300° C.

* * * * *